(12) United States Patent
White et al.

(10) Patent No.: US 9,993,167 B2
(45) Date of Patent: Jun. 12, 2018

(54) APPARATUS AND METHOD FOR SENSOR DEPLOYMENT AND FIXATION

(71) Applicant: PACESETTER, INC., Sylmar, CA (US)

(72) Inventors: Jason White, Smyrna, GA (US); Jin Woo Park, Suwanee, GA (US)

(73) Assignee: St. Jude Medical Luxenbourg Holdings II S. A. R. L ("SJM LUX II"), Luxembourg (LU)

( * ) Notice: Subject to any disclaimer, the term of this patent is extended or adjusted under 35 U.S.C. 154(b) by 511 days.

(21) Appl. No.: 14/567,974

(22) Filed: Dec. 11, 2014

(65) Prior Publication Data

US 2015/0201885 A1    Jul. 23, 2015

Related U.S. Application Data

(60) Provisional application No. 61/963,675, filed on Dec. 11, 2013.

(51) Int. Cl.
*A61B 5/02* (2006.01)
*A61B 5/0215* (2006.01)
*A61B 5/00* (2006.01)

(52) U.S. Cl.
CPC .......... *A61B 5/0215* (2013.01); *A61B 5/6876* (2013.01); *A61B 5/6884* (2013.01); *A61B 5/0031* (2013.01); *A61B 5/686* (2013.01); *A61B 2560/0219* (2013.01); *A61B 2560/066* (2013.01)

(58) Field of Classification Search
CPC ... A61B 5/0215; A61B 5/6876; A61B 5/6884; A61B 2560/066; A61B 2560/0219; A61B 5/0031; A61B 5/686
See application file for complete search history.

(56) References Cited

U.S. PATENT DOCUMENTS

| | | | |
|---|---|---|---|
| 6,416,474 B1 * | 7/2002 | Penner | A61B 5/0031 600/309 |
| 8,475,372 B2 * | 7/2013 | Schell | A61B 5/6876 600/309 |
| 2002/0151816 A1 * | 10/2002 | Rich | A61B 5/0031 600/547 |
| 2006/0287602 A1 * | 12/2006 | O'Brien | A61B 5/0031 600/486 |
| 2014/0074155 A1 * | 3/2014 | Rothstein | A61B 17/0057 606/213 |

* cited by examiner

*Primary Examiner* — Tiffany Weston
*Assistant Examiner* — Tho Tran

(57) ABSTRACT

A delivery and fixation system of an implant assembly having an intracorporeal device. The system provides for a low profile delivery system for an implant assembly having an anchor for fixation within a vessel adapted to be delivered via a catheter.

11 Claims, 2 Drawing Sheets

APPARATUS AND METHOD FOR SENSOR DEPLOYMENT AND FIXATION

PRIORITY CLAIM

This application claims priority to U.S. Provisional Patent Application Ser. No. 61/963,675, filed Dec. 11, 2013.

BACKGROUND

The ability to measure a patient's physiologic parameters in a repeatable and accurate manner using implanted sensor devices is an important advancement in the treatment and management of disease. Due to size constraints of a patient's cardiovascular system, there is a continuous desire to downsize the implants in order to minimize issues associated with its presence. As smaller size sensors are imagined, complications may be associated with a loss in signal strength. Standard LC (inductor/capacitor) resonant based sensor technology often uses a non-magnetic material (e.g., a material with low magnetic permeability such as fused silica, vacuum, air, kapton) for the inductor coil core within the body of the sensor making up the inductor. However, as the size of the sensor decreases and sensors are implanted in more distant locations, there is a need to increase signal strength in order to effectively communicate with external devices outside of the patient's body. Moreover, there is an additional need for smaller sensors so that they can be implanted in locations that cannot accommodate conventional, relatively large sensors. One such sensor is that which incorporates ferromagnetic materials within the core of the sensor, increasing the magnetic permeability of the core and the overall signal strength from the inductor, thereby allowing for a relatively small sensor footprint.

The decrease in size of intracorporeal devices necessitates alternate delivery tools and the use of lower profile delivery systems. Thus, a need exists for improved delivery devices to accommodate lower profile implants.

SUMMARY

The following description is provided as an enabling teaching of the disclosure in its best, currently known embodiment. To this end, those skilled in the relevant art will recognize and appreciate that many changes can be made to the various aspects of the disclosure described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof. U.S. Pat. No. 8,355,777 is herein incorporated by reference.

As used throughout, the singular forms "a," "an" and "the" include plural referents unless the context clearly dictates otherwise. Thus, for example, reference to "an assembly" can include two or more such assemblies unless the context indicates otherwise. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. As used herein, the terms "optional" or "optionally" mean that the subsequently described event or circumstance can or cannot occur, and that the description includes instances where said event or circumstance occurs and instances where it does not. As used herein, the terms "optional" or "optionally" mean that the subsequently described event or circumstance can or cannot occur, and that the description includes instances where said event or circumstance occurs and instances where it does not.

One embodiment disclosed herein is directed toward apparatus, systems and methods to facilitate accurate implantation of an implant and, optionally, short- and long-term monitoring of the pressure within a body cavity via the implant. For example, one or more embodiments of the present invention include one or more devices placed within a body cavity or vessel for the purposes of providing pressure readings. For example, a cylindrically shaped intracorporeal sensor device is releasably attached to the end of an implant assembly by way of a pair of loops and a guidewire that collectively define an engagement assembly. The decrease in delivery size and the resulting puncture site to access the vascular system correlates to a decrease in recovery times and a lower rate of complications associated with accessing the vasculature.

Sensors may be delivered to the implant site by pushing through an introducer or catheter which has an inner diameter large enough to pass the sensor through at least the distal end thereof. With this implant method, the sensor may be simply pushed out the distal end of the introducer or catheter using an inner implant catheter to advance the sensor past the distal end of the introducer. The sensor does not need to be coupled to the inner catheter or may be attached only on the back end of the sensor.

In one embodiment the delivery system for securing, delivering and deploying an implant assembly includes an engagement assembly comprising a first lumen in an implant catheter adapted to accept a guidewire, and a fixed loop extending from the distal end of the implant catheter. The fixed loop is adapted to slide over and engage a corresponding loop structure on the implant, and the guidewire may be extended from the distal end of the delivery catheter and threaded through the loop structure on the implant to lock the respective loop structures together. When the guidewire is retracted such that it no longer threads through the loop structure on the implant, the respective loops can be disengaged, thereby allowing the implant to release from the distal end of the implant catheter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the Figures are not drawn to scale, and that elements of similar structure or function are generally represented by like reference numerals for illustrative purposes throughout the Figures. These drawings depict only typical embodiments of the invention and are not therefore to be considered to be limiting of its scope, the invention will be described and explained with additional specificity and detail through the use of the accompanying drawings. In alternate non-limiting embodiment the relative size, shape and location of the sensor can be changed. In another alternate non-limiting embodiment the sensor can be directly wired to the receiver or the receiver can be located in close proximity to or directly to the patient to provide additional mobility during continuous monitoring of cavity pressure.

DETAILED DESCRIPTION

Figure 1:
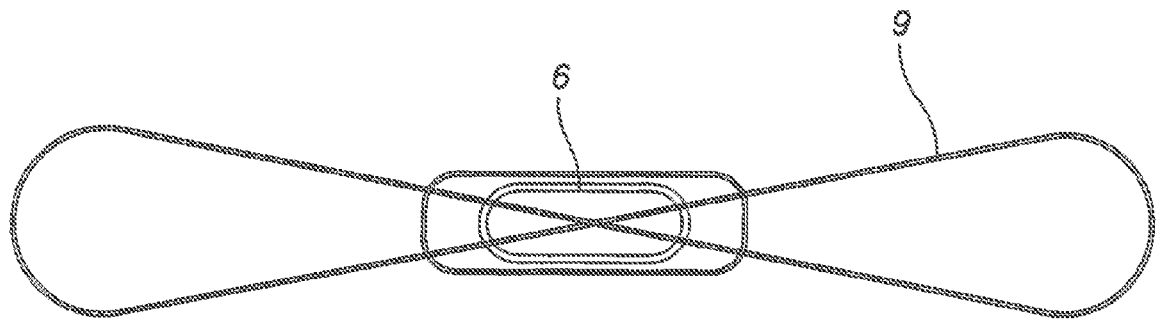
FIG. 1 is one non-limiting embodiment of the disclosed apparatus illustrating the top view of an intracorporeal sensor device and wire fixation loops.

The foregoing summary, as well as the following detailed description of certain embodiments, will be better understood when read in conjunction with the appended drawings. It should be understood that the various embodiments are not limited to the arrangements and instrumentality shown in the drawings. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale. In the following description, numerous specific details are set forth in order to provide a thorough understanding of the present invention. It will be obvious, however, to one skilled in the art that the present disclosure may be practiced without these specific details.

One or more embodiments generally relate to apparatus and methods for sensor deployment. As shown in FIG. 1, an implantable sensor 6 with fixation loops 9 is provided for implant within a patient at a desired site, for example in the patient's vasculature. The fixation loops 9 may be formed from metal or polymer, and may be in the form of a wire structure. In an alternative embodiment, rather than fixation loops the fixation structure may be in the form of radial wire array structures, daisy petal structures, and other such structures.

Figure 2:
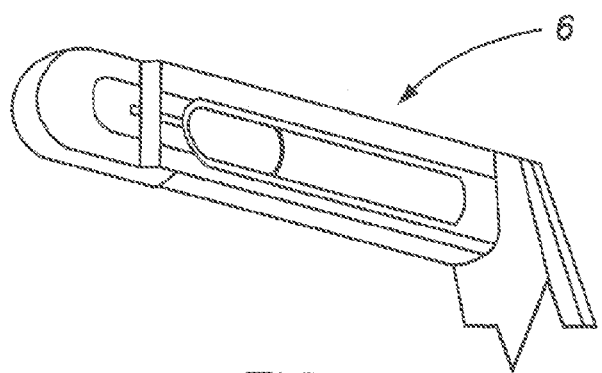
FIG. 2 is one non-limiting embodiment of an intracorporeal device illustrating the inner ferrite core of the device permitting smaller devices and lower profile implant assemblies.

In one embodiment, the sensor 6 is adapted for implantation within the patient's pulmonary artery. As shown in FIG. 2, the sensor 6 may be formed with a ferromagnetic core around which an inductor of the LC circuit is wound and then connected to capacitor, which as described in more detail below provides for improved signal strength of the LC circuit relative to a non-ferrous core. This allows for a relatively small overall footprint of the sensor body while still providing the ability to reliably communicate with an external transceiver.

In some embodiments, the sensors consist of a passive electromagnetically resonant circuit. In yet another aspect, the sensors can comprise transponders capable of actively transmitting a signal with a, for example, particular signal strength, frequency or phase and the position of the tracked objects can be determined through processing of the relative values.

Figure 3:
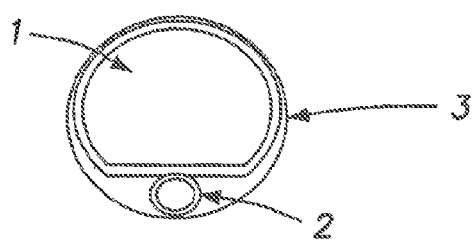
FIG. 3 is one non-limiting embodiment of the cross section of the implant assembly illustrating the inner diameter of the implant sheath, the intracorporeal device space and lumen for receiving a delivery catheter.

Referring now to FIG. 3, a delivery sheath or introducer 3 is shown, which defines a first lumen 1 and a second lumen 2. The first lumen 1 is adapted to receive the sensor 6 and an implant catheter 8, as described in more detail below. The second lumen 2 is adapted to receive a delivery catheter therethrough.

The first lumen 1 is sized to accommodate the sensor body at at least the distal end thereof. It will be apparent to those skilled in the art that the first lumen 1 may taper down at some distance from the distal end of the sheath 3, in which case the sensor 6 can be loaded into the first lumen 1 through the distal end thereof, with the implant catheter extending through the tapered first lumen 1 to the proximal end of the sheath 3. Alternatively, the first lumen 1 may have a constant diameter along the entire length of the sheath 3, in which case the sensor 6 may be advanced from the proximal end of the sheath through the first lumen to the distal end thereof, by using the implant catheter 8 as described below.

Figure 4:
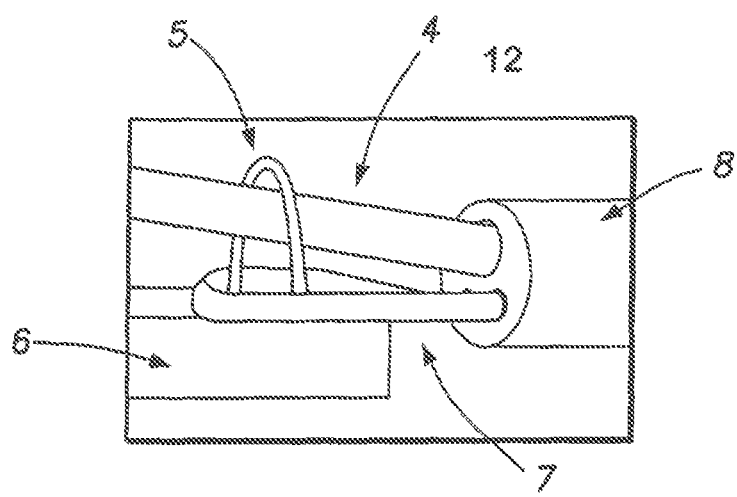
FIG. 4 is one non-limiting embodiment of the implant assembly illustrating an implant assembly catheter, guide wire, intracorporeal device, a fixed loop of the intracorporeal device and fixed loop of the implant assembly defining the engagement assembly.
Figure 5:
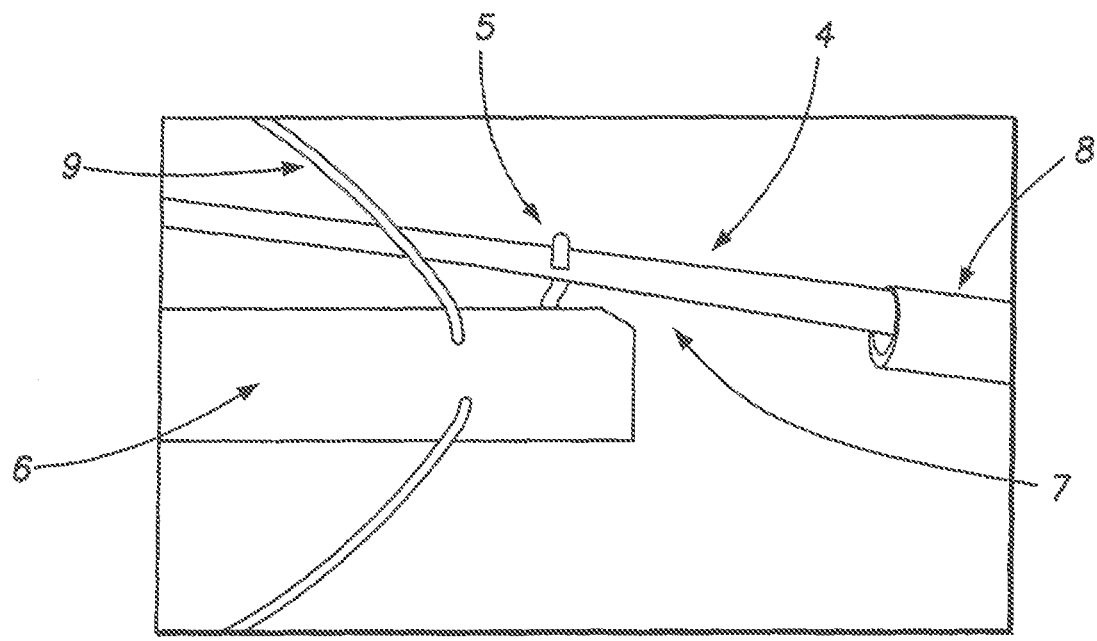
FIG. 5 is one non-limiting embodiment of the implant assembly illustrating the implant assembly catheter, guide wire, intracorporeal device, fixed loop of the intracorporeal device, fixed loop of the implant assembly defining the engagement assembly.

Referring now to FIGS. 4 and 5, the details of the engagement assembly will be described. The implant catheter 8 is formed with a guidewire lumen 12 through which a guidewire 4 may be advanced from the distal end of the catheter 8. Also provided on the distal end of catheter 8 is a loop structure 7. Sensor 6 includes a corresponding loop 5, with loop structure 7 being sized and configured to slide over loop 5. Guidewire 4 can then be advanced past the distal end of catheter 8 and threaded through loop 5 to lock the loops together.

The engagement assembly provides a delivery system for securing, delivering and deploying intracorporeal sensor device 6. The loop structure 7 may be mounted on the distal end of delivery catheter 8, or alternatively may extend through a second lumen formed in catheter 8, which allows for advancing and retracting the loop structure 7.

In one embodiment, the implant assembly obstructs no more than approximately 50% or less of the cross-sectional area of the vessel in which it resides. Preferably, the implant assemblies obstruct 20% or less of the cross-sectional area of the vessel. Minimizing the obstruction of flow within the vessel allows the sensor to remain secured in position in a vessel without creating significant impact to the flow within the vessel.

In one embodiment, as shown in FIGS. 1 and 2, the body of the intracorporeal device 6 coupled to the fixation loops 9 has a width of about 0.5 to about 4 mm, a height of about 0.5 to about 4 mm, and a length of about 0.5 to about 25 mm. Examples of such devices are disclosed in commonly owned patents U.S. Pat. No. 6,855,115; and in co-pending, commonly owned application Ser. Nos. 10/054,671; 10/886,829; 10/215,377; 10/215,379; 10/943,772 incorporated herein by reference.

One method of deploying and fixing an implant assembly according to this invention is described below. The delivery system, consisting of catheter 8 and sensor 6, is loaded into the vessel introducer 3 and navigated to the deployment site. The delivery system length can be increased or decreased according to standard practice depending on the access site chosen. In one embodiment, the deployment site is a vessel, and may be any artery or arteriole in the pulmonary artery vasculature. After the assembly is oriented to a preferred orientation, the sensor 6 is deployed by retracting the guidewire 4 so that it no longer is threaded through the fixed loop 5 of the sensor 6. Upon deployment, the sensor 6 is allowed to "float" in the vasculature and is carried by blood flow until it reaches a bifurcation in the vasculature. The fixation loops 9 prohibit the intracorporeal device from progressing into smaller vessels, thereby lodging the sensor at a location that is immediately proximal to the bifurcation. The delivery tools are then removed from the body.

The present invention can thus be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A system for deploying a sensor into a vessel at a location, the system comprising:
   an introducer that defines at least one lumen;
   an implant catheter adapted to be received in the at least one lumen, the implant catheter comprising a guidewire lumen and an engagement loop;
   a sensor comprising at least one fixed loop, wherein the engagement loop is configured to be slid over the fixed loop;
   a guidewire to pass through the guidewire lumen and to be threaded through the fixed loop in order to releasably lock the engagement loop and the fixed loop together;
   wherein the implant catheter and sensor are adapted to be housed within the at least one lumen of the introducer and wherein the implant catheter is advanceable through the at least one lumen to advance the sensor from the distal end of the introducer.

2. The system of claim 1, wherein the sensor comprises a pressure sensor.

3. The system of claim 1, wherein the sensor is adapted to be permanently fixed relative to the operative location in the vessel.

4. The system of claim 1, wherein the sensor further comprises at least one fixation loop.

5. The system of claim 1, wherein the introducer further defines a second lumen configured to receive a delivery catheter therein.

6. The system of claim 1, wherein the sensor comprises a pressure sensor that comprises an inductor and a capacitor.

7. The system of claim 6 wherein the sensor comprises a ferromagnetic core around which at least a portion of the inductor is wound.

8. The system of claim 1, wherein the engagement loop is mounted on a distal end of the implant catheter.

9. The system of claim 1, wherein the engagement loop is advanceable relative to the implant catheter.

10. The system of claim 1, wherein the at least one lumen of the introducer is isodiametric.

11. The system of claim 1, wherein a closed intermediate portion of the fixed loop is to extend through the engagement loop and the guide wire is to be threaded through the intermediate portion of the fixed loop in order to lock the fixed and engagement loops together.

* * * * *